United States Patent [19]

Schwarzer et al.

[11] Patent Number: 4,548,708

[45] Date of Patent: Oct. 22, 1985

[54] PROCESS FOR REMOVING HYDROGEN SULFIDE FROM NATURAL GAS, OIL AND MIXTURES THEREOF

[75] Inventors: Hans Schwarzer, Wolfratshausen; Werner Meisel, Geretsried, both of Fed. Rep. of Germany

[73] Assignee: Peroxid-Chemie GmbH, Höllriegelskreuth, Fed. Rep. of Germany

[21] Appl. No.: 446,087

[22] Filed: Dec. 1, 1982

[30] Foreign Application Priority Data

Dec. 23, 1981 [DE] Fed. Rep. of Germany ....... 3151133

[51] Int. Cl.$^4$ .................... C10G 27/04; C01B 17/033
[52] U.S. Cl. ................ 208/196; 208/208 R; 423/224; 210/759
[58] Field of Search .......................... 208/196, 208 R; 423/224; 210/759

[56] References Cited

U.S. PATENT DOCUMENTS

| | | | |
|---|---|---|---|
| 2,744,054 | 5/1956 | Pieters | 208/196 |
| 3,506,572 | 4/1970 | Van Dyke et al. | 252/8.55 E |
| 3,647,683 | 3/1972 | Kelly | 208/196 |

FOREIGN PATENT DOCUMENTS

| | | | |
|---|---|---|---|
| 18635 | 11/1980 | European Pat. Off. | 423/224 |
| 2504484 | 8/1976 | Fed. Rep. of Germany | 210/759 |

OTHER PUBLICATIONS

Ayling et al, "Waste Treatment with $H_2O_2$", Chemical Engineering, pp. 79–82, Nov. 30, 1982.

Sugano et al, "Process for Treating Bed-Odor Gas", Japanese Patent Public Disclosure, 16664/75, Feb. 21, 1975.

Primary Examiner—D. E. Gantz
Assistant Examiner—Chung K. Pak
Attorney, Agent, or Firm—Felfe & Lynch

[57] ABSTRACT

A process is provided for substantially complete elimination of hydrogen sulphide from the organic phase of natural gas, crude oil or mixtures thereof, by reaction with aqueous hydrogen peroxide in the absence of any catalyst or organic compounds or of compounds that yield them at a pressure of at least 90 kPa gage. The process is particularly useful with crude materials as they are pumped directly from the earth.

7 Claims, No Drawings

PROCESS FOR REMOVING HYDROGEN SULFIDE FROM NATURAL GAS, OIL AND MIXTURES THEREOF

BACKGROUND

The invention relates to the elimination of hydrogen sulphide from natural gas, crude oil, and mixtures thereof.

It is well known that crude oil or natural gas frequently contains considerable amounts of hydrogen sulphide. Since hydrogen sulphide has a strong corrosive effect on the equipment with which the natural gas or crude oil comes in contact, and is, moreover, highly toxic, it must be eliminated. The elimination of hydrogen sulphide from natural gas using acetic acid and hydrogen peroxide in the presence of a catalyst is already well known. In this method, it can be assumed that peracetic acid is the active reagent, as it is formed from acetic acid and hydrogen peroxide under the conditions described in the prior art. It is also known that other organic per acids can be used to eliminate hydrogen sulphide from gaseous hydrocarbons. However, complete elimination of the hydrogen sulphide was not possible. It is also known that injecting hydrogen peroxide together with an alkali or alkaline earth hydroxide into geothermal steam will reduce the hydrogen sulphide content. But again, complete elimination of the hydrogen sulphide has not been accomplished in this manner. From EU-AS No. 29, 472, it is also known that liquid hydrocarbons can be treated with an aqueous solution of hydrogen peroxide and a metal ion catalyst such as iron (III) chloride and copper (II) chloride, to eliminate sulphur compounds.

In contrast to the prior art, the object of the invention is the development of a process for the simple elimination of hydrogen sulphide from natural gas and crude oil or mixtures thereof, which will require neither catalyst nor organic additives, while permitting the complete elimination of hydrogen sulphide from the hydrophobic gaseous or liquid phase. Furthermore, the inventive method can be carried out under the conditions which frequently occur in the extraction of natural gas or crude oil from the ground.

The object of the invention is accomplished in a process for the elimination of hydrogen sulphide from natural gas, crude oil and mixtures thereof, which is characterized in that an aqueous hydrogen peroxide solution is added at elevated pressure and, in some cases, elevated temperature to the watery natural gas, crude oil or mixtures thereof pumped from the ground; and reacted in a reactor with mixing and with the maintenance of the elevated pressure, at least until the desired reduction of the hydrogen sulphide content is complete.

DESCRIPTION OF THE INVENTION

Surprisingly, it has been found that it is possible under the conditions in accordance with the invention, to eliminate undesirable hydrogen sulphide entirely from the organic phase, solely with hydrogen peroxide, without the addition of any catalysts or organic compounds or of compounds that yield them. This was unexpected because the inventive method involves a multi-phase system with the hydrogen sulphide being eliminated from a hydrophobic organic phase and the reagent being present in the aqueous phase. In contrast, the prior art teaches at best a 98% elimination of hydrogen sulphide in a *single* phase reaction when hydrogen peroxide is used in combination with alkali hydroxide and catalytically active metal ions.

The pressure maintained during the inventive process reaction should be at least 90 kPa gage, although slightly lower pressures can, under certain circumstances, be used. Preferably, a gage pressure of approximately 500 to approximately 2,000 kPa is applied. Thus, with gas or oil which is being delivered under pressure, it is possible to inject the hydrogen peroxide solution directly into the high-pressure line.

In the process of the invention, the temperature can be varied within wide limits. However, it is preferable to avoid an excessively high temperature at which spontaneous decomposition of the hydrogen peroxide is promoted. Temperatures between 0° and 60° C., preferably between 20° and 40° C., are generally appropriate.

The reactors can be those known for this purpose. Tubular reactors are preferred, since the required degree of mixing of the phases can be easily controlled by the flow rate and the inside diameter of the tube. Also, the reaction time (resident time) can be easily controlled by the flow rate. A section of the high-pressure pipe, for example, can serve as a tubular reactor. In such a reactor, aqueous hydrogen peroxide solution would be injected at the upstream end and the residual hydrogen sulphide content measured *at the downstream end* the rate at which the hydrogen peroxide is injected can be controlled on the basis of this measurement.

Other types of reactor can also be used, requiring only that they achieve satisfactory mixing of the hydrophobic phase with the aqueous phase by means of suitable mixing apparatus, and can maintain the pressure for the required reaction time. The reaction time normally depends on the applied pressure, the temperature, and the effectiveness of the mixing. In the preferred pressure and temperature range, and using a tubular reactor, a complete elimination of hydrogen sulphide can be achieved, as a rule, with a reaction period between about 5 and about 20 minutes.

The amount of hydrogen peroxide injected is preferably such that it is completely consumed in the reaction, i.e., any excess of hydrogen peroxide is avoided. The investigations carried out have shown that, normally, at least 20 ml of hydrogen peroxide in the form of a 35% aqueous solution should be added for each gram of hydrogen sulphide to be eliminated. Most appropriately, the hydrogen peroxide is added in the form of a concentrated solution, particularly a 20 to 50% solution. However, the concentration can be considerably lower, particularly if the natural gas or crude oil contains very little water. Preferably 50 to 500 ml of a 35% solution of hydrogen peroxide is used per gram of hydrogen sulphide present in the organic phase.

The invention makes it possible to eliminate hydrogen sulphide completely from the organic phase of natural gas or crude oil mixtures. Since neither organic additives nor catalysts are needed, little work is required. Furthermore, the difficulties encountered in the controlled input of catalysts, which cannot be added directly to the hydrogen peroxide before introduction into the reaction vessel because of the danger of decomposition, are avoided.

EXAMPLES

Example 1

60 to 65 $m^3$ of natural gas and approximately 3.5 to 4 $m^3$ of watery crude oil are delivered per hour in the form of a mixture from an oil well. The temperature is 30° to 40° C., the pressure at the wellhead is 800 to 1100 kPa gage.

The hydrogen sulphide content averaged 250 mg/m$^3$.

Using a high-pressure injection pump, 0.5 liter per hour of 35% aqueous hydrogen peroxide solution was injected into the high-pressure line at wellhead. This mixture of gas, oil and water is pumped from the oil well, which has a depth of approximately 3,500 m, via a high-pressure pipeline with an inside diameter 80 mm to a treatment plant about 2,000 meters away, where the gas is separated from the liquid in a separator and introduced into a city gas supply piping system. From the separator, the liquid passes into a separating tank where the water is separated from the oil. The oil then goes to the refinery, the water to a purification plant.

At the end of the high-pressure line, ahead of the point at which it enters the treatment plant, the hydrogen sulphide content is measured by means of an automatic, commercially available hydrogen sulphide analyzer which operates by the colorimetric method of measurement using strips of test paper and lead acetate as indicator.

The residence time of the mixture of gas, crude oil and water in the high-pressure pipe is approximately 45 minutes. In the course of a test under practical conditions over a period of several days, the amount of hydrogen sulphide determined at the end of the pipe was 0 mg/m$^3$.

Example 2

In the manner described in Example 1, hydrogen peroxide was added to another oil well where the mixture of gas, crude oil and water being delivered contained an average of 165 mg of hydrogen sulphide per m$^3$. The rate of hydrogen peroxide injection, the composition of the mixture, the pressure, the temperature and the distance were approximately the same as in Example 1.

The rate of injection of hydrogen peroxide in the form of 35% aqueous solution was increased until the hydrogen sulphide content measured at the end of the high-pressure pipe was steady at 0 to 5 mg/m$^3$. The rate of injection at that time was 2.5 liters per hour.

We claim:

1. A process for substantially complete elimination of hydrogen sulfide from the organic phase of natural gas, crude oil or mixtures thereof, consisting essentially of the step of reacting, by mixing, the natural gas, crude oil or mixture thereof, with an aqueous reagent consisting essentially of 20 to 50% aqueous hydrogen peroxide, without the addition of any catalysts or organic compounds or of compounds that yield them, at a pressure of at least about 90 kPa gage and a reaction temperature of up to the decomposition temperature of hydrogen peroxide to remove the hydrogen sulfide from the organic phase.

2. The process of claim 1 wherein the pressure used is 500 to 2000 kPa gage.

3. The process of claim 2 wherein the reaction temperature of 0° C. to 60° C. is maintained.

4. The process of claim 1 wherein the reaction temperature of 0° C. to 60° C. is maintained.

5. The process of claim 1 wherein the mixing is accomplished in a tubular reactor and is required by the flow rate therethrough.

6. The process of claim 1 wherein the aqueous hydrogen peroxide is added directly to natural gas, crude oil or mixtures thereof as they are pumped from the ground and, after reaction, the aqueous phase is separated and removed.

7. The process of claim 1 wherein approximately 20 ml of said 20 to 50% aqueous hydrogen peroxide is added per gram hydrogen sulphide.

* * * * *

UNITED STATES PATENT AND TRADEMARK OFFICE
CERTIFICATE OF CORRECTION

PATENT NO. : 4,548,708

DATED : October 22, 1985

INVENTOR(S) : Schwarzer et al.

It is certified that error appears in the above-identified patent and that said Letters Patent is hereby corrected as shown below:

Claim 5, line 2, "required" should be -- regulated --.

Signed and Sealed this

Eighteenth Day of February 1986

[SEAL]

Attest:

DONALD J. QUIGG

Attesting Officer

Commissioner of Patents and Trademarks